United States Patent [19]
Allen et al.

[11] Patent Number: 5,389,794
[45] Date of Patent: Feb. 14, 1995

[54] SURFACE PIT AND MOUND DETECTION AND DISCRIMINATION SYSTEM AND METHOD

[75] Inventors: Nicholas C. Allen, Bedford; Sergey V. Broude, Newton Centre, both of Mass.; Eric T. Chase, Nashua, N.H.; Pascal Miller, North Chelmsford, Mass.; Jay L. Ormsby, Salem, N.H.; Bruno Rostaing, Medford; Lloyd P. Quackenbos, Newburyport, both of Mass.

[73] Assignee: QC Optics, Inc., Burlington, Mass.

[21] Appl. No.: 981,745

[22] Filed: Nov. 25, 1992

[51] Int. Cl.[6] ............................................. G01N 21/88
[52] U.S. Cl. ..................................... 250/572; 356/237
[58] Field of Search ................... 250/562, 572, 563; 356/430, 431, 237

[56] References Cited

U.S. PATENT DOCUMENTS

| | | | |
|---|---|---|---|
| 4,092,068 | 5/1978 | Lucas et al. | 250/572 |
| 4,395,122 | 7/1983 | Southgate et al. | 250/572 |
| 4,412,743 | 11/1983 | Eberly | 356/237 |
| 4,794,264 | 12/1988 | Quachenbos et al. | 250/572 |
| 4,794,265 | 12/1988 | Quackenbos et al. | 250/572 |
| 4,920,385 | 4/1990 | Clarke et al. | 356/237 |
| 4,943,734 | 7/1990 | Johnson et al. | 250/572 |
| 5,153,844 | 10/1992 | Beni et al. | 356/237 |
| 5,155,371 | 10/1992 | Burggraf et al. | 356/431 |
| 5,189,481 | 2/1993 | Jann et al. | 250/572 |

Primary Examiner—David C. Nelms
Assistant Examiner—Stephone B. Allen
Attorney, Agent, or Firm—Tandiorio & Teska

[57] ABSTRACT

A surface pit and mound detection and discrimination system including a device for scanning a beam of radiation over a surface, and a mechanism for detecting a local slope on the surface for differentiating between whether the beam of radiation is scanning a pit or a mound on the surface.

20 Claims, 4 Drawing Sheets

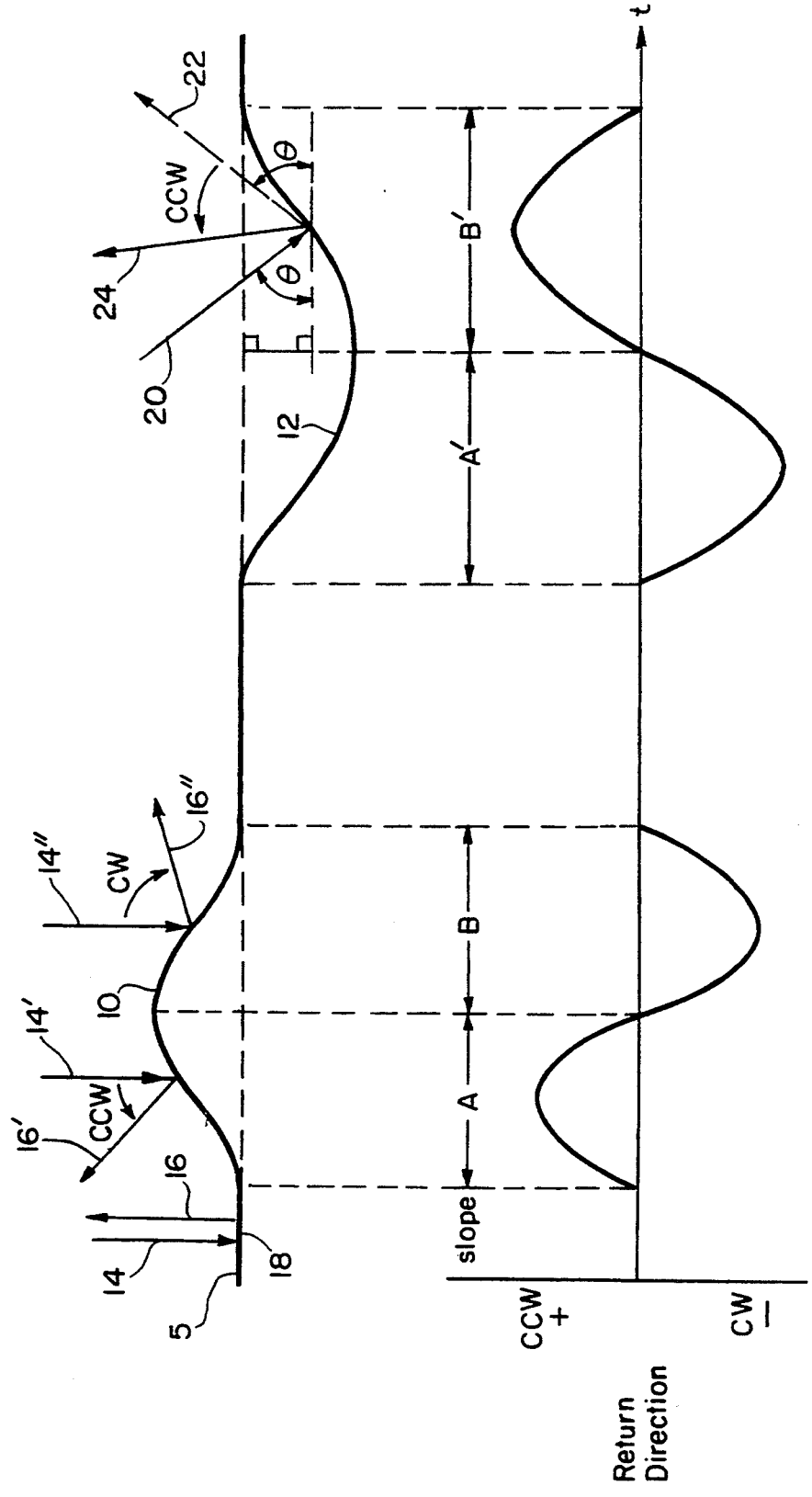

SURFACE PIT AND MOUND DETECTION AND DISCRIMINATION SYSTEM AND METHOD

FIELD OF INVENTION

This invention relates to an optical technique and system for uniquely detecting pits and mounds on a smooth surface and discriminating between them, determining the relative height of a mound or depth of a pit above and below the surface, and establishing the transverse extent of the pit or mound on the surface.

BACKGROUND OF INVENTION

There is a significant quality control problem associated with two classes of surface imperfections known as pits and mounds. These may occur, for example, on nickel-plated aluminum substrates used in the manufacture of thin-film magnetic media, but may pose a problem with respect to any smooth surface.

Surface pits are local depressions, and surface mounds are local protrusions of the surface with respect to its average level around the imperfection. They are but two classes of flaws that can be encountered. Others include defects, large and small of other morphology, including scratches, excessive surface roughness, digs, as well as contaminants of various natures including dirt, dust, oil, fingerprints, and the like. Defects on the surface of a rigid magnetic media may be either the result of an impingement onto the surface, or of a deposition of a foreign material on the surface, or of a tearing of material away from the surface, or of a combination of these phenomena.

Both the surface pits and surface mounds of interest have diameters of between a few micrometers to several hundred micrometers and depths (or heights) of a few hundredths to one micrometer typically. Both pits and mounds may be smooth or contain breaks or craters on their surface.

There are devices known which detect flaws generally, and which distinguish between pits and flaws caused by scratches and other flaws such as surface contamination including dirt or oil and the like. Reference is made to U.S. Pat. Nos. 4,794,264; 4,943,734; and 4,794,265, assigned to the same assignee as the instant application, and incorporated as if fully set forth herein by this reference.

Distinguishing between a pit and a mound, however, once such a flaw is detected, is useful in many applications. For example, a magnetic head used to write information on a magnetic disk could be damaged by a mound, whereas only a loss of information would result as the magnetic head passes over a pit. Technological advances have been made to the extent that the magnetic head quickly passes over the disk at an elevation of only a few microinches, (0.05-0.1 micrometers). Hence, a mound rising to an elevation higher than even a few hundredths of a micrometer could severely damage the head.

The equipment embodying the patents referenced above would automatically determine that a flaw exists generally, but the operator must still use a microscope to inspect the surface and determine whether an individual flaw is a pit or a mound, and also to determine, for a mound, whether it rises to an elevation which could cause damage to a magnetic head. Such inspection is time consuming, subject to error, and could result in further contamination due to the handling required. Moreover, such inspection is subjective in that it will not always be readily apparent whether a given mound rises in elevation to the point where magnetic head damage could occur. In short, such inspection is unreliable.

SUMMARY OF INVENTION

It is therefore an object of this invention to provide a system which is capable of both detecting surface pits and mounds and distinguishing between them.

It is a further object of this invention to provide such a surface pit and mound detection and discrimination system and method which eliminates the need for human inspection to either detect surface pits and mounds or to distinguish between them.

It is a further object of this invention to provide such a surface pit and mound detection and discrimination system which is capable of evaluating whether a surface protrusion (mound) detected rises to an elevation which could damage equipment passed over the surface.

It is a further object of this invention to provide such a surface pit and mound detection and discrimination system which measures the relative height of a mound above, and the depth of a pit below the surface; and also measures the transverse extent of either of these defects on the surface.

This invention results from the realization that since pits and mounds on a surface have different shape profiles, a beam of radiation traversing a pit will be reflected differently than a beam traversing a mound, and if the reflections are monitored as the beam traverses the surface, the changes in direction of the slope of the flaw represented by the change in direction of the reflected beams will enable a pit to be distinguished from a mound, and also that the time dependence of the strength of the signal indicating the detection of a pit or mound can be used to ascertain the elevation of the mound above the surface or the depression of a pit below the surface, as well as the transverse extent of a pit or mound on the surface.

This invention features a surface pit and mound detection and discrimination system comprising means for scanning a beam of radiation over a surface, means for detecting a local slope on the surface, and means, responsive to the means for detecting, for differentiating between whether the beam of radiation is scanning a pit or a mound. The means for differentiating may include means for indicating the presence of a pit on the surface in response to a change in slope in one manner, and for indicating the presence of a mound on the surface in response to a change in slope in a different manner. The means for scanning may include a laser source and means for providing relative motion between the laser beam of the laser source and the surface. Relative motion between the surface and the beam of radiation may include means for rotating the surface and translating the surface. In a preferred embodiment, there are means For directing a laser beam in a direction normal to the surface. The means for detecting may also include means for sensing radiation reflected from the surface and for indicating a deviation from the path expected for a nominal surface representative of a local slope on a surface. The means for detecting may also include sensor means, responsive to radiation reflected from the surface in the specular region, having a first output for a deviation indicative of a positive slope on the surface and a second output for a deviation indicative of a negative slope on a surface. In this embodiment, the means for differentiating may include output means denoting the presence of a mound (pit) on the surface when a period of deviations indicative of a positive (negative) slope are proximately followed by a series of deviations indicative of a negative (positive) slope.

There may also be means for measuring the relative height of a mound or depth of a pit on the surface in response to radiation reflected from the surface as well as the transverse extent of either a pit or a mound on the surface. The means for scanning may include means for denoting the location of a mound or a pit on the surface.

This invention also features a surface pit and mound detection and discrimination system comprising means for directing a beam of radiation to a surface, means for providing relative motion between the beam and the surface, sensor means for detecting the reflected radiation of the surface for determining any deviation of the reflected radiation from the path expected for a nominal surface, and for producing at least one signal representative of whether the beam directed to the surface is traversing the positive or negative slope of a defect on the surface. Finally, there are means, responsive to the sensor means, for distinguishing whether the defect is a pit or a mound in response to a change of slope on the surface. The means for providing relative motion between the beam and surface may include means for controlling the location of the directed beam on the surface for establishing the location of a defect on the surface. There may be also means for monitoring the surface area covered by a detected mound, and the strength of the signal representative of whether the beam directed to the surface is traversing a positive or a negative slope of a defect on the surface, for establishing the relative depth (height) of a detected pit (mound).

This invention further includes a method for detecting pits or mounds on a surface and discriminating between them comprising scanning a beam of radiation over a surface, detecting a local slope on the surface, and differentiating between whether the beam of radiation is scanning a pit or a mound. The step of differentiating between whether the beam of radiation is scanning a mound or a pit may include indicating the presence of a pit on the surface in response to a change in slope in one manner and a mound on the surface in response to a change in slope in a different manner. Finally, this invention features a method of detecting pits and mounds on a surface and discriminating between them comprising directing a beam of radiation to a surface, providing relative motion between the beam and the surface, detecting reflected radiation from the surface, determining any deviation of the reflected radiation from the path expected for a nominal surface, producing a signal representative of whether the beam directed to the surface is traversing a positive or negative slope on the surface, and distinguishing whether the beam directed to the surface is traversing a pit or a mound in response to a change in slope on the surface. Further included may be the step of analyzing the relative strength of the signals representative of whether the beam directed to the surface is traversing a positive or a negative slope on the surface as well as the time which it takes for the beam of radiation to traverse the positive and negative slopes of a pit or mound on the surface for measuring the relative depth or height of it below or above the surface.

A laser may be used in conjunction with various other optical devices as the means for scanning a beam of radiation over the surface in conjunction with means to rotate and translate the surface. The means for detecting a local slope on the surface may include one or more sensors which detect radiation in specular region and which also detect deviation of the reflected radiation from the path expected for a nominal surface. The output of the sensor system may be indicative of whether a local slope detected on the surface is upward (positive) sloping, or downward (negative) sloping. These signals may be analyzed by electronic means for differentiating between whether the beam of radiation is scanning a pit or a mound.

DISCLOSURE OF PREFERRED EMBODIMENT

Other objects, features and advantages will occur to those skilled in the art from the following description of a preferred embodiment and the accompanying drawings, in which:

FIG. 2 is a schematic diagram of the profiles of a pit and a mound on a surface such as a magnetic disk also showing the reflective paths of an illumination beam traversing these defects;

FIG. 3 is a plot of the relative slopes of the pit and the mound depicted in FIG. 2 and also showing the direction of deflection of the reflected beam with respect to the illumination beam as determined according to this invention;

Figure 1:
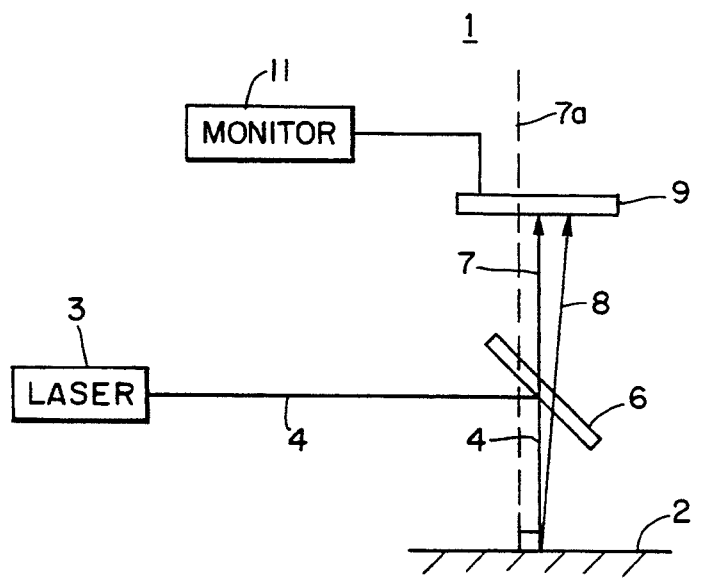
FIG. 1 is a schematic diagram of a pit and mound detection and discrimination system according to this invention.

This invention may be accomplished by a system 1, FIG. 1, including laser 3 which directs a beam of radiation 4 via beam splitter 6 perpendicular to surface 2. If there is no defect at the point where beam 4 strikes surface 2, the reflected beam 7 strikes detector system 9 without any deviation from perpendicular 7a to surface 2 according to Snell's law. However, if beam 4 strikes the local slope of a pit or mound, as is more fully discussed below in reference to FIG. 2, the reflected beam 8 deviates from normal 7a to surface 2 and this deviation is detected by detector system 9. Monitoring device 11, responsive to detector system 9, may monitor changes in the direction of deviation as beam 4 traverses surface 2 to provide an indication whether beam 4 is traversing a protrusion (mound) or depression (pit) as is explained below.

Mound 10, FIG. 2, on surface 5, and pit 12 have different profiles, resulting in different slope patterns, FIG. 3. Mound 10 has a positive slope in region A and a negative slope in region B. Pit 12 has the reverse slope pattern: negative first in region A', then positive in region B'. Accordingly, an illumination beam of light normal to surface 5 represented by vector 14 is reflected in a specular fashion on the nominal or defect-free portion 18 of surface 5, and there is no appreciable deviation of the reflected beam 16 from the path of illumination beam 14. Although the illuminating radiation beam is referred to herein as light, electromagnetic radiation of any suitable wavelength may be used. As illumination beam 14' traverses the positive slope of mound 10, however, the reflected beam 16' deviates in a direction counterclockwise to illumination beam 14' until the apex of mound 10 is encountered where the slope changes from positive to negative. At the apex, there is again no appreciable deviation of the reflected beam with respect to the illumination beam. Along the negative slope, reflected beam 16" deviates in a direction clockwise from illumination beam 14". The reverse is true for pit 12: counterclockwise deviation first in Region A'; clockwise deviation in Region B'.

The result is that the direction of deviation, clockwise or counterclockwise, plotted for the reflected beam as the illumination beam traverses mound 10 and pit 12 is similar the slope patterns for mound 10 and pit 12, respectively. As shown in FIG. 2, counterclockwise deviations correspond to an illumination beam passing over a positive slope; clockwise deflections correspond to an illumination beam passing over a negative slope: a counterclockwise deviation followed proximately by a clockwise deviation is indicative of a mound while a clockwise deviation followed proximately by a counterclockwise deviation is indicative of a pit.

If the illumination beam is caused to strike surface 5 in a direction which is not normal to the surface, the respective reflected beams are still reflected according to Snell's law. Accordingly, the deviation of the reflected beam from the expected path of reflection, had the illumination beam been traversing a nominal defect-free surface, may be still monitored in an equivalent fashion and the resulting slope curves appear similar to those shown in FIG. 3. For example, illumination beam 20, FIG. 2, is directed at angle $\theta$ to nominal defect-free surface 5. The expected non-defect return path according to Snell's law is reflected beam 22, also at angle $\theta$ to nominal defect-free surface 5. Due to pit 12, however, the actual reflected beam 24 deviates in a direction counterclockwise from expected reflected beam 22.

Accordingly, in general, the direction of deviation of the reflected beam from the path expected for a nominal surface determines, over time as the illumination beam traverses the surface, whether the illumination beam is traversing a mound or a pit. A counterclockwise deviation first followed by a clockwise deviation indicates the presence of a mound; a clockwise deviation first followed by counterclockwise deviation indicates the presence of a pit. An assumption is made that the velocity of the illumination point motion as it moves along the surface is uniform. As used herein, "the reflected beam" means all radiation in the reflected direction within the numerical aperture equal to the numerical aperture of the illumination beam, and various optical devices may be incorporated to focus the illumination beam accordingly.

Figure 4:
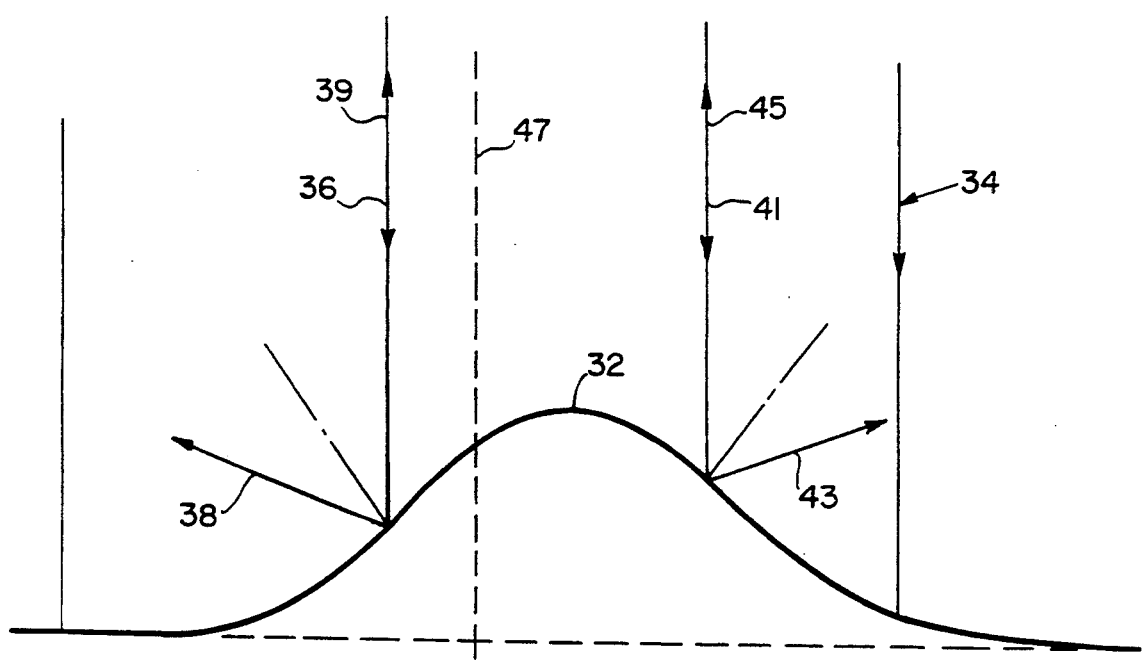
FIG. 4 is a schematic diagram of the reflective characteristics of only portions of an illumination beam when the illumination beam footprint is greater in area than the defect being detected according to this invention.

In some cases, the illumination beam footprint may cover most or even the entire defect, for example, mound 32, FIG. 4. Individual rays of beam 34, however, notably ray 36, are reflected (as shown by ray 38) in a path different from path 39, the expected path had beam 34 been traversing a nominal surface without the presence of mound 32. The intensity distribution across the cross section of beam 34 is such that there is a higher intensity on the beam 34 axis 47, and lower intensity on the beam 34 periphery, typically symmetrical Gaussian distribution. As the result, the total intensity of rays deflected counterclockwise (similar to the ray 36/38 in FIG. 4) will be higher than the total intensity of the rays deflected clockwise (similar to the ray 41/43), as long as the axis 47 of the beam 34 intersects the positive slope of mound 32, as in FIG. 4. Consequently, monitoring device 11 of FIG. 1 will correctly indicate presence of a positive slope. Similarly, when axis 47 of the beam 34 intersects negative slope of mound 32, the intensity of light deflected clockwise will be higher than the intensity of light deflected counterclockwise and the monitor 11 will correctly indicate the presence of a negative slope. Thus, monitor 11 of FIG. 1 can still adequately determine whether beam 34 is traversing a pit or a mound according to this invention. This can still be adequate to determine whether beam 34 is traversing a pit or a mound according to this invention.

Figure 5:
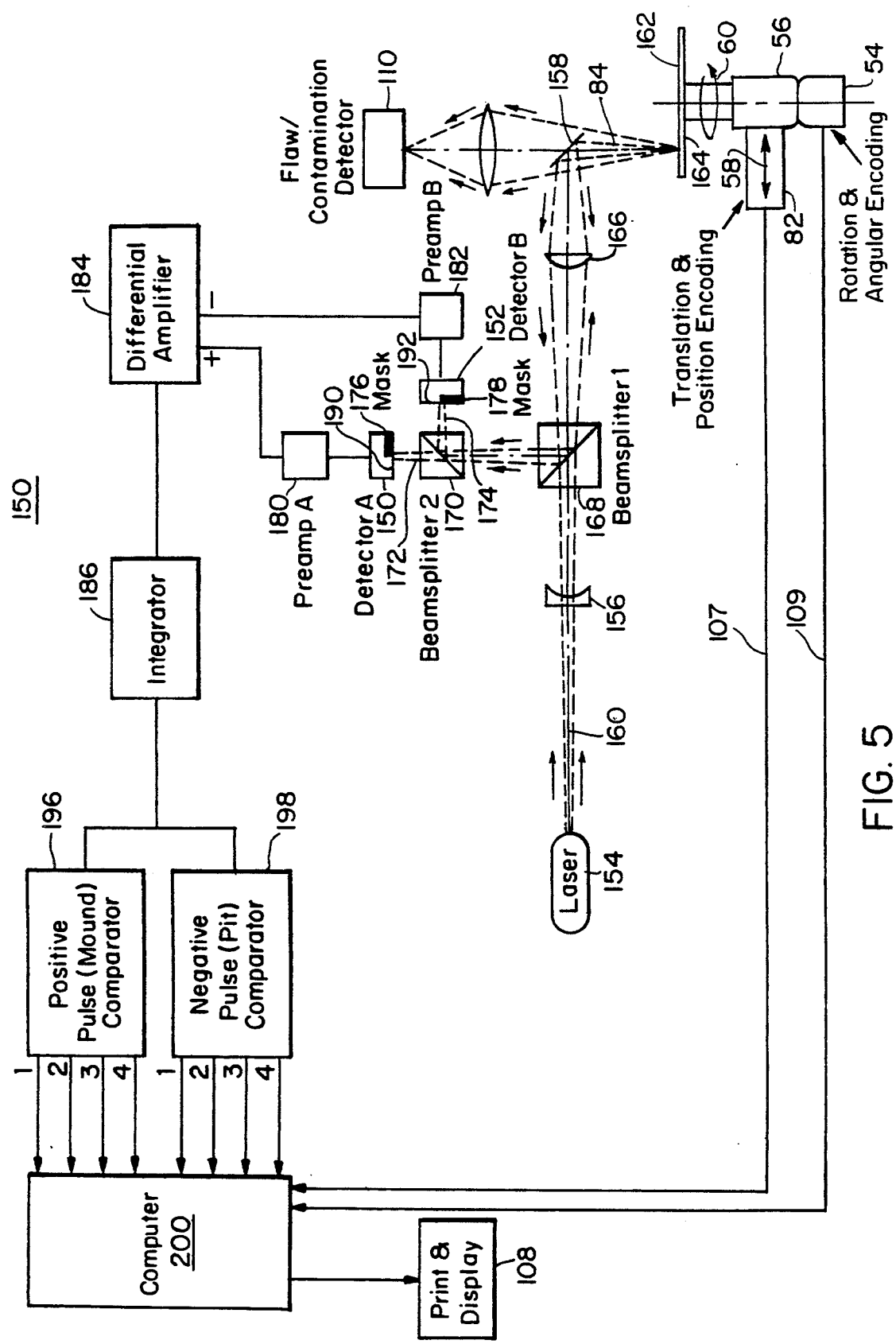
FIG. 5 is a block diagram of an embodiment of a surface pit and mound detection and discrimination system according to this invention.

One implementation of system 1 is shown in greater detail in FIG. 5, where surface pit and mound detection and discrimination system 150 includes laser 154 for directing beam 160 through beam expander 156 to mirror 158 which directs beam 160 to surface 162 of specimen 164. Specimen 164 may be in the form of an aluminum blank, a polished, or even a coated magnetic disk: system 150 of this invention allows inspection during nearly all processing stages to detect defects early before further costly fabrication processes occur.

Encoder 54 monitors and controls the angular position of air spindle 56. Servo motor 82 moves air spindle 56 in a translational manner back and forth in the direction shown by arrow 58. Air spindle 56 rotates specimen 164 as indicated by arrow 60. In this way, beam 160 traverses or scans surface 162. The rotation of spindle 56 and its translation occur simultaneously and the rates of these two motions are selected with the size of the spot of beam 160 on surface 162 so that the entire surface 162 of specimen 164 is covered by the spiral path of the spot. Accordingly for every pit or mound of interest, there is a portion of this spiral path which passes through the center of the defect. Computer 200 drives motor 82 and receives position input over line 107. Computer 200 also monitors encoder 54 and receives positional information over line 109. Printout unit or display 108 thus provides an indication of any pits or mounds detected as well as the size of the detected pit or mound.

If there is no defect at the point where beam 160 strikes surface 162, and if surface 162 is a highly polished surface, all radiation is typically reflected specularly back along beam 84. In this case, the beam reverses its path to mirror 158, lens 166 and beam splitter 168 to beam splitter 168 and beam splitter 170 where it is divided into two beams 172 and 174. Beam 174 impinges on detector 152; beam 172 impinges on detector 150. Each of the detectors has a semi-annular sensitive area and a central stop positioned so that the beams, when they arrive after reflection from an undisturbed surface 162 of specimen 164 are blocked and not detected.

Any non-specular scattering from surface 162, produced by defects other than the pits or mounds of interest, is sensed by flaw detector 110 according to the methodology and device as described in U.S. Pat. No. 4,794,265. Finally, the print and display unit 108 displays the location of any mounds or pits detected on specimen 164 as well as signals indicative of whether the defect detected is a pit or a mound, and the relative heights of any mounds detected above nominal surface 162 of specimen 164. In this way, quality control personnel may evaluate each mound to determine whether subsequent magnetic head damage would occur as the magnetic head writes information to specimen 164 by passing over surface 162 at distances as low as even a fraction of a micrometer above surface 162.

However, if a pit or mound is encountered, the portion of beam 160 which arrives at the slope region of the defect deviates away from normal to surface 162. The deviating reflected beam passes via mirror 158, lens 166, and beam splitters 168 and 170, and the deviation corresponds (in terms of FIG. 5) to the offset of the reflected beam left and right on the surface of detector 150, and to the offset of the reflected beam up and down on the surface of detector 152. Detectors 150 and 152 are equipped with masked areas 176 and 178, respectively, which cover opposite halves of detectors 150 and 152 so that when the beam deviates due to the local slope of surface 162, it arrives onto the sensitive area of one detector and is blocked by the mask on the other detector.

The outputs of detectors 150 and 152 are amplified by pre-amplifiers 180 and 182, respectively, and applied to differential amplifier 184, where a difference of these two signals is formed. If a mound is encountered by the beam 160, the slope of surface 162 changes in accordance with the slope profile shown in FIG. 3. Accordingly, as illumination beam 160 traverses the positive slope of a mound, the reflected beam deviates to impinge upon the unmasked sensitive portion 190 of detector 150, but impinges on the masked portion 178 of detector 152. As illumination beam 160 traverses the apex of a mound, there is no deviation and the reflected beam impinges upon the masked portion of both detectors 150 and 152. As illumination beam 160 traverses the negative slope of a mound, the deviation of the reflected beam impinges upon the masked portion 176 of detector 150, and upon the unmasked portion 192 of detector 152, resulting in a signal delivered from detector 152 to pre-amplifier 182. The output of differential amplifier 184 is supplied to integrator 186 which produces a positive pulse for mounds and negative pulses for pits. From FIG. 3 it can be seen that the integral of a mound slope profile—positive slope followed by negative slope—(or integral of the beam deflection vs. time), is positive, while this integral for a pit (negative slope followed by positive one) is negative. The output of integrator 186 is supplied to two sets of comparators, comparator 196 responding to positive pulses, comparator 198 to negative pulses. These comparators are monitored by computer 200 together with position and angular encoding signals, thus providing data for defect identification, sizing and mapping.

Figure 7:
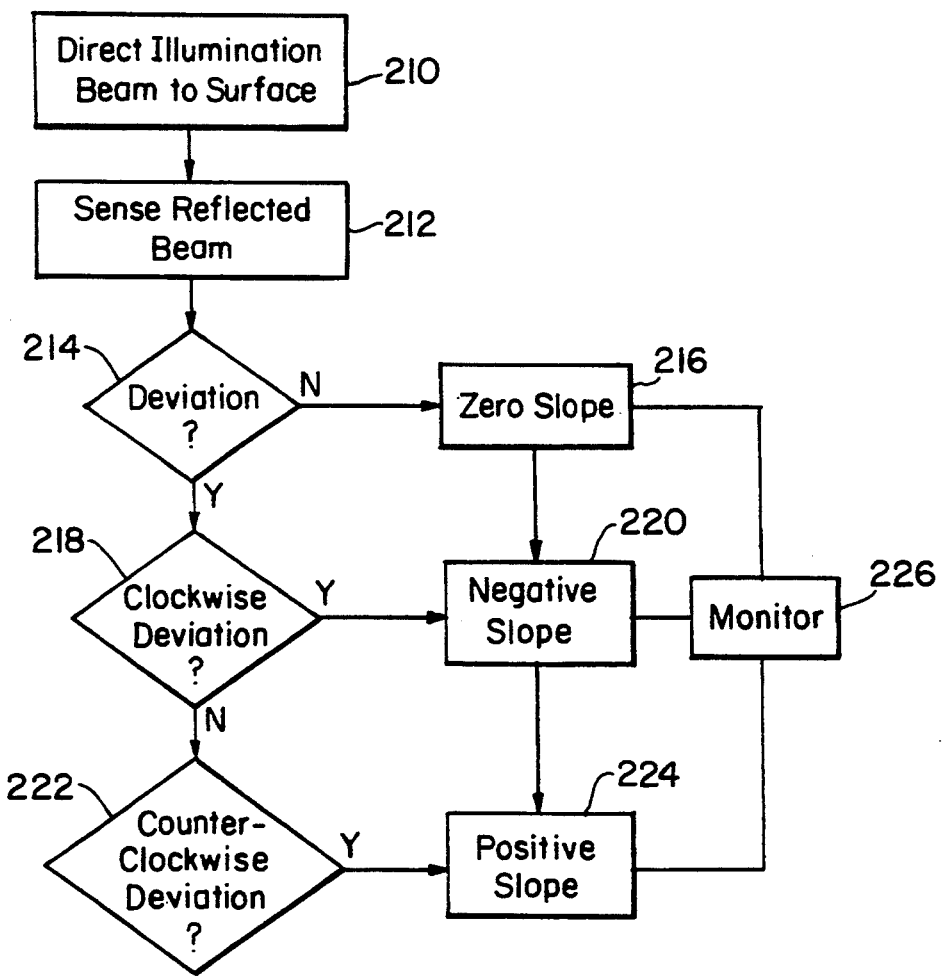
FIG. 7 is a block diagram of a method of detecting pits and mounds according to this invention and discriminating between them.

The technique according to this invention constitutes directing an illumination beam to a surface, step 210, FIG. 7. The reflected beam is sensed, step 212, and it is determined whether any deviation has occurred from the expected reflection path for a defect-free surface, step 214. If there is no deviation, the slope is determined to be zero, step 216. If there is clockwise deviation, step 218, the slope is determined to be negative, step 220. Counterclockwise deviation, step 222, indicates a positive slope, step 224. Monitoring these deflections, step 226, over time as the illumination beam traverses the defect allows an evaluation to be made as to whether the illumination beam is traversing a pit or a mound.

A prototype system according to this invention was used to inspect a number of various magnetic hard disks. The outputs of the dual detector monitor the slope of the disk surface illuminated by the laser spot (beam diameter equals approximately 30 micrometers at $1/e^2$ intensity level). When the laser beam scans the disk and crosses a pit or a mound, the deviation of the laser beam is successfully detected and the direction of this deviation enables discrimination between a pit and a mound. The outputs of the detectors are electronically processed in order to get a signal which qualitatively represents the surface profile. The prototype electronic circuit processes, digitizes and transfers data to a computer. A modified experimental DISKAN 7000 available from QC Optics, Inc. of Burlington, Mass., is able to collect a map of the disk in either pit or mound detection modes. The normal channel of the DISKAN 7000 was left unchanged and was used for the collection of contamination maps of the disks. The DISKAN 7000 is equipped with a microscope to review defects detected on the maps. Using the microscope images, simple surface defects are qualitatively described and categorized, but as discussed in the Background of Invention above, little quantitative information is available by this technique. Furthermore, when the defects have complex shapes, the interpretation of the microscope images becomes difficult. Some of the more complex defects were therefore further analyzed using a WYKO® interference microscope. Color surface profile plots, three-dimensional plots, and cross-sectional two-dimensional plots provided by the WYKO® interferometer made it possible to unambiguously and qualitatively describe the size and the shape of these pits and mounds. This detailed analysis of each defect was then correlated to the data obtained using the modified DISKAN 7000 according to this invention. It was shown that a good correlation existed between the data obtained by using the modified DISKAN 7000 according to this invention in pit and mound detection channels, and the microscope analysis performed on each defect. In particular, the mounds and pits that appear smooth and symmetric in the microscope, are exclusively detected in the mound and pit channels. For the defects which were detected both in the pit and in the mound channels, microscope data confirmed that both a mound above, and a pit below, the average surface level were present next to each other. The detection limit of the mound channel is better than 0.06 micrometer. The detection limit of the pit channel was set at a slightly higher level, around 0.09 micrometer At these detection levels, the foreign contaminants on the disk surface do not seem to give significant detection in the pit or mound channels and are detected exclusively by scattering in the contamination channel according to the patents referenced in the Background of the Invention. The performance of the modified DISKAN 7000, pit and mound detection techniques according to this invention proved to offer good sensitivity toward small pits and small mounds.

Figure 6:
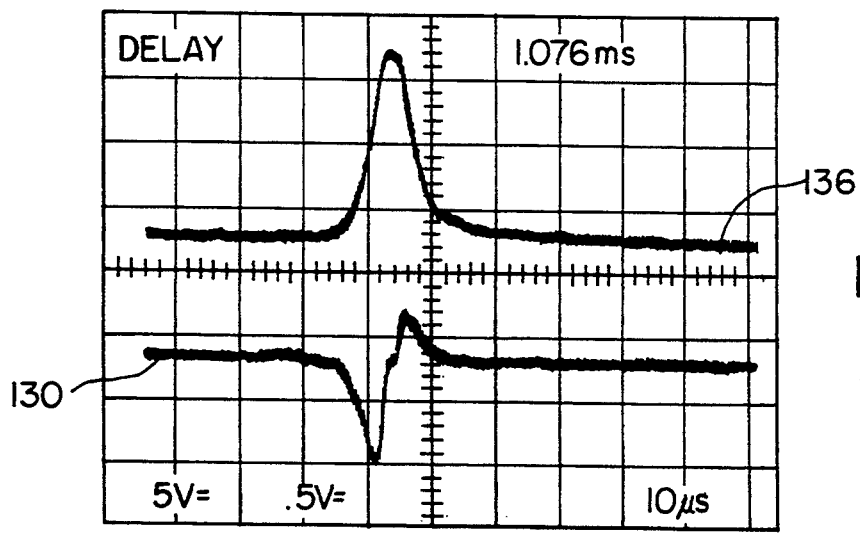
FIG. 6 is a picture of the actual output of a system according to this invention for a beam traversing a mound on a magnetic disk.

For example, in display 108, FIG. 5, when beam 160, traversed a mound on a magnetic disk, signal 130, FIG. 6, was produced which corresponds to the slope profile for a mound, FIG. 3. The amplitude of the signal and the time which it takes for the illuminating beam to traverse both the positive and negative slopes of a mound are used to deduce the relative size of the mound. The amplitude of integrator 186, FIG. 5, signal 136, FIG. 6, is indicative of the defect's depth or height while the time duration is indicative of the defect's transverse extent.

Although specific features of this invention are shown in some drawings and not others, this is for convenience only as some feature may be combined with any or all of the other features in accordance with the invention. Other embodiments will occur to those skilled in the art and are within the following claims:

What is claimed is:

1. A surface defect pit and mound detection and discrimination system comprising:
   means for scanning a beam of radiation over a surface;
   means for separately sensing radiation scattered from the surface in the near-specular region and in the far specular region for differentiating between pits and mounds and other types of defects;
   means for detecting a local slope on the surface from radiation scattered from the surface in the near-specular region; and
   means, responsive to said means for detecting, for differentiating between whether said beam of radiation is scanning a pit or a mound.

2. The surface defect pit and mound detection system of claim 1 in which said means for differentiating includes means for indicating the presence of a pit on the surface in response to a change in slope in one manner and a mound on the surface in response to a change in slope in a different manner.

3. The surface defect pit and mound detection and discrimination system of claim 1 in which said means for scanning includes a laser source and means for providing relative motion between the laser beam and the surface.

4. The surface pit and mound detection and discrimination system of claim 3 in which means for providing relative motion includes means for rotating said surface and translating said surface in relation to the laser beam.

5. The surface pit and mound detection and discrimination system of claim 1 in which said means for scanning includes means for directing a laser beam in a direction normal to the surface.

6. The surface pit and mound detection and discrimination system of claim 1 in which said means for detecting includes first and second detectors for sensing radiation reflected from the surface, each said detector disposed and masked for separately indicating a deviation in one direction from the path expected for a nominal surface representative of a local slope on the surface.

7. The surface pit and mound detection and discrimination system of claim 1 in which said means for detecting includes sensor means, responsive to radiation reflected from the surface in the specular region, having a first output for a deviation of said reflected radiation indicative of a positive slope on the surface and a second output for a deviation indicative of a negative slope on the surface.

8. The surface pit and mound detection and discrimination system of claim 7 in which said means for differentiating includes output means denoting the presence of a mound on the surface when a deviation indicative of a positive slope is proximately followed by a deviation indicative of a negative slope.

9. The surface pit and mound detection and discrimination system of claim 1 further including means, responsive to said means for detecting, for measuring the relative height of a mound on the surface in response to radiation reflected from the surface.

10. The surface pit and mound detection and discrimination system of claim 1 further including means, responsive to said means for detecting, for assessing the relative depth of a pit on the surface in response to radiation reflected from the surface.

11. The surface pit and mound detection and discrimination system of claim 1 further including means, responsive to said means for detecting, for ascertaining the transverse extent of a pit and mound detected on the surface.

12. The surface pit and mound detection and discrimination system of claim 1 in which said means for scanning includes means for denoting the location of the pit or mound on the surface.

13. A surface pit and mound detection and discrimination system comprising:
    means for directing a beam of radiation to a surface;
    means for providing relative motion between said beam and the surface;
    means for separately sensing radiation scattered from the surface in the near-specular region and in the far-specular region for differentiating between pits and mounds, and other types of defects;
    sensor means for detecting reflected radiation from the surface in the near-specular region for determining any deviation of said reflected radiation from the path expected for a nominal surface, and for producing at least one signal representative of whether said beam directed to the surface is traversing the positive or negative slope of a defect on the surface; and
    means, responsive to said sensor means, for distinguishing whether said defect is a pit or a mound in response to a change of slope on the surface.

14. The surface pit and mound detection and discrimination system of claim 13 in which said means for providing relative motion between said beam and the surface includes means for controlling the location of said directed beam on the surface for establishing the location of a defect on the surface.

15. The surface pit and mound detection and discrimination system of claim 13 further including means for monitoring the surface extent of a detected pit or mound, and the strength of said signal representative of whether said beam directed to the surface is traversing a positive or negative slope of a defect on the surface, for establishing the relative height of a detected mound and the depth of a detected pit.

16. A method of detecting pits and mounds on a surface and discriminating between them, comprising:
    scanning a beam of radiation over a surface;
    separately sensing radiation scattered through the surface in the near-specular region and in the far-specular region for differentiating between pits and mounds, and other types of defects;
    detecting a local slope on the surface from radiation scattered from the surface in the near-specular region; and
    differentiating between whether said beam of radiation is scanning a pit or a mound.

17. The method of claim 16 in which differentiating between whether said beam of radiation is scanning a pit or a mound includes indicating the presence of a pit on the surface in response to a change in slope in one manner and a mound on the surface in response to a change in slope in a different manner.

18. A method of detecting pits and mounds on a surface and discriminating between them, comprising:
    directing a beam of radiation to a surface;

providing relative motion between the beam and the surface;

detecting reflected radiation from the surface including separately sensing radiation scattered from the surface in the near-specular region and in the far-specular region for differentiating between pits and mounds, and other types of defects;

determining any deviation of the reflected radiation from radiation scattered from the surface in the near-specular region from the path expected for a nominal surface;

producing a signal representative of whether the beam of radiation directed to the surface is traversing a positive or negative slope on the surface; and distinguishing whether the beam directed to the surface is traversing a pit or a mound in response to a change in slope on the surface.

19. The method of detecting pits and mounds on a surface and discriminating between them of claim 18 further including analyzing the relative strength of said signals representative of whether the beam directed to the surface is traversing a positive or a negative slope on the surface and the time in which it takes for the beam of radiation to traverse the positive and negative slopes of a pit or mound on the surface for measuring the relative height of any detected mound and the relative depth of any detected pit below the surface.

20. A surface defect pit and mound detection and discrimination system comprising:

means for scanning a beam of radiation over a surface;

means for detecting a local slope on the surface including first and second detectors for sensing radiation reflected from the surface, each said detector disposed and masked for separately indicating a deviation in one direction from the path expected for a nominal surface representative of a local slope on the surface; and means, responsive to said means for detecting, for differentiating between whether said beam of radiation is scanning a pit or a mound.

* * * * *

UNITED STATES PATENT AND TRADEMARK OFFICE
CERTIFICATE OF CORRECTION

PATENT NO. : 5,389,794
DATED : Feb. 14, 1995
INVENTOR(S) : Allen et al.

It is certified that error appears in the above-indentified patent and that said Letters Patent is hereby corrected as shown below:

On the title page, Attorney, Agent, or Firm, change "Tandiorio" to --Iandiorio--.

Signed and Sealed this

Second Day of May, 1995

Attest:

BRUCE LEHMAN

*Attesting Officer*    *Commissioner of Patents and Trademarks*